United States Patent [19]

Leveen

[11] 4,058,126
[45] Nov. 15, 1977

[54] DEVICE FOR THE FRACTURE OF THE BLOOD VESSEL LINING

[76] Inventor: Harry H. Leveen, 800 Poly Place, Brooklyn, N.Y. 11209

[21] Appl. No.: 385,075

[22] Filed: Aug. 2, 1973

[51] Int. Cl.² .......................................... A61B 17/32
[52] U.S. Cl. .................................................... 128/305
[58] Field of Search .............................. 128/305, 346

[56] References Cited

U.S. PATENT DOCUMENTS

| 2,074,214 | 3/1937 | Edmonson | 128/305 |
| 2,618,270 | 11/1952 | Pearson, Jr. | 128/346 |
| 3,182,373 | 5/1965 | Strand | 128/346 UX |

OTHER PUBLICATIONS

Wylie, "A New Aorta Clamp," Surgery, 364: 781-783, 1954.

*Primary Examiner*—Channing L. Pace

[57] ABSTRACT

A device for the selective fracture of the inner lining or tunica intima of a blood vessel without severing of the surrounding outer layer or tunica adventitia of the vessel is disclosed. The device comprises a combination of an anvil member having a dull blade affixed thereto which acts as one blade of a guillotine which descends upon the vessel caught between it and a hammer member of the guillotine. The hammer member is spring loaded through connection with a slider arm which extends upward toward the spring and a grip for the fingers of the user. There is provided a guide for the anvil and its blade which guide is aligned and connected with the central rod which extends between the slider arm and the spring which causes impact on the hammer member of the guillotine. The central rod acts as a core for two springs which surrounds the same. The first spring is referred to as a proximal compression spring and the second spring is referred to as distal actuator spring which is located peripherally to the proximal compression spring. The action of the first compression and the release of these two springs causes a shock to extend down the central rod or core into the slider arm and hence into the hammer portion of the guillotine. This shock action follows a first closing of the opening between the anvil and the hammer of the guillotine and is of such controlled momentum that it causes the dull blade of the anvil to fracture the inner layer of the blood vessel without severing the outer muscular layers of the blood vessel.

3 Claims, 4 Drawing Figures

DEVICE FOR THE FRACTURE OF THE BLOOD VESSEL LINING

BACKGROUND OF THE INVENTION

In the art of vascular surgery it is often desired to remove the inner layer which is fatty in nature from a vessel without cutting the vessel entirely through at a certain point but nevertheless cutting the inner layer to such a degree that at a point some distance away the blood vessel can be opened and the inner sleeve so to speak can be pulled out of the vessel.

In an effort to solve this problem applicant began experiments in the design of an instrument which would meet this need since no device was presently available to enable vascular surgeons like himself to perform this frequently needed procedure. The first step that the method requires is a holding in place of the blood vessel at the spot selected for the internal fracture of the inner layer of the blood vessel. This was achieved by the creation of a guillotine-like arrangement with an upper anvil member which contained a dull blade resting on one side of the blood vessel and a hammer-like opposing jaw which held the blood vessel therebetween. The next problem was to apply only that pressure to the pincers of the guillotine that would be sufficient to cut the softer inner layer of the blood vessel but leave intact the tougher outer muscular layer of the blood vessel. This was achieved by positioning two springs around a central rod or core which connected to the hammer member of the guillotine on one end and a pressure retaining handle on the other. When these springs were first impressed by sliding them toward the guillotine hammer and then suddenly released to snap back an impact sharply against a protuberance of the rod, the shock wave generated was transmitted down the rod and into the hammer with only sufficient momentum to cause a controlled cutting or severance of the vessel. Therefore as a result of this process of thought and design there was created a new instrument which shall be described in greater detail by the following written description and reference to the several drawings and pictorial representations of the device. The several objects of the invention will become clear from a reading of the specification and need not be more specifically elaborated at this point although it should be pointed out that a surgical method as well as a new surgical instrument comprises the subject matter of this invention.

BRIEF DESCRIPTION OF THE INVENTION

Accordingly there is described herein a new device for the partial fracture of various layered vessels such as blood vessels. This device will be described more particularly by reference to the several FIGS. 1 through 4 of the attached drawing.

Figures 2, 4:
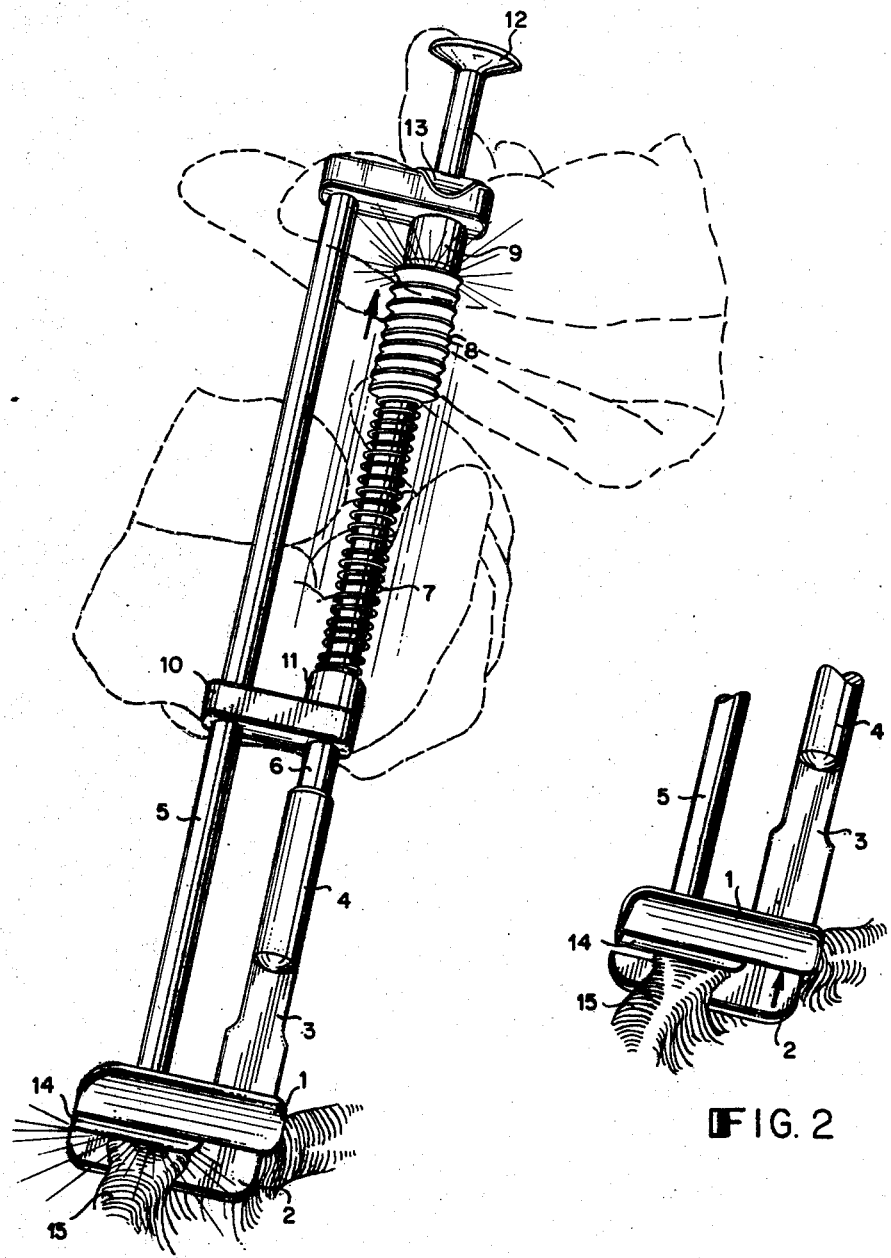
FIG. 2 shows the hammer and the anvil members of the guillotine closed about a blood vessel which is squeezed therein.

Finally, FIG. 4 shows the perspective view of the last step of the cutting operation wherein the compression spring members are suddenly released so that they snap back and create an impact which travels along the central core and is transmitted to the hammer portion of the guillotine.

The invention will now be explained in greater detail by specific reference to FIGS. 1 through 4 of the drawing.

Figures 1, 3:
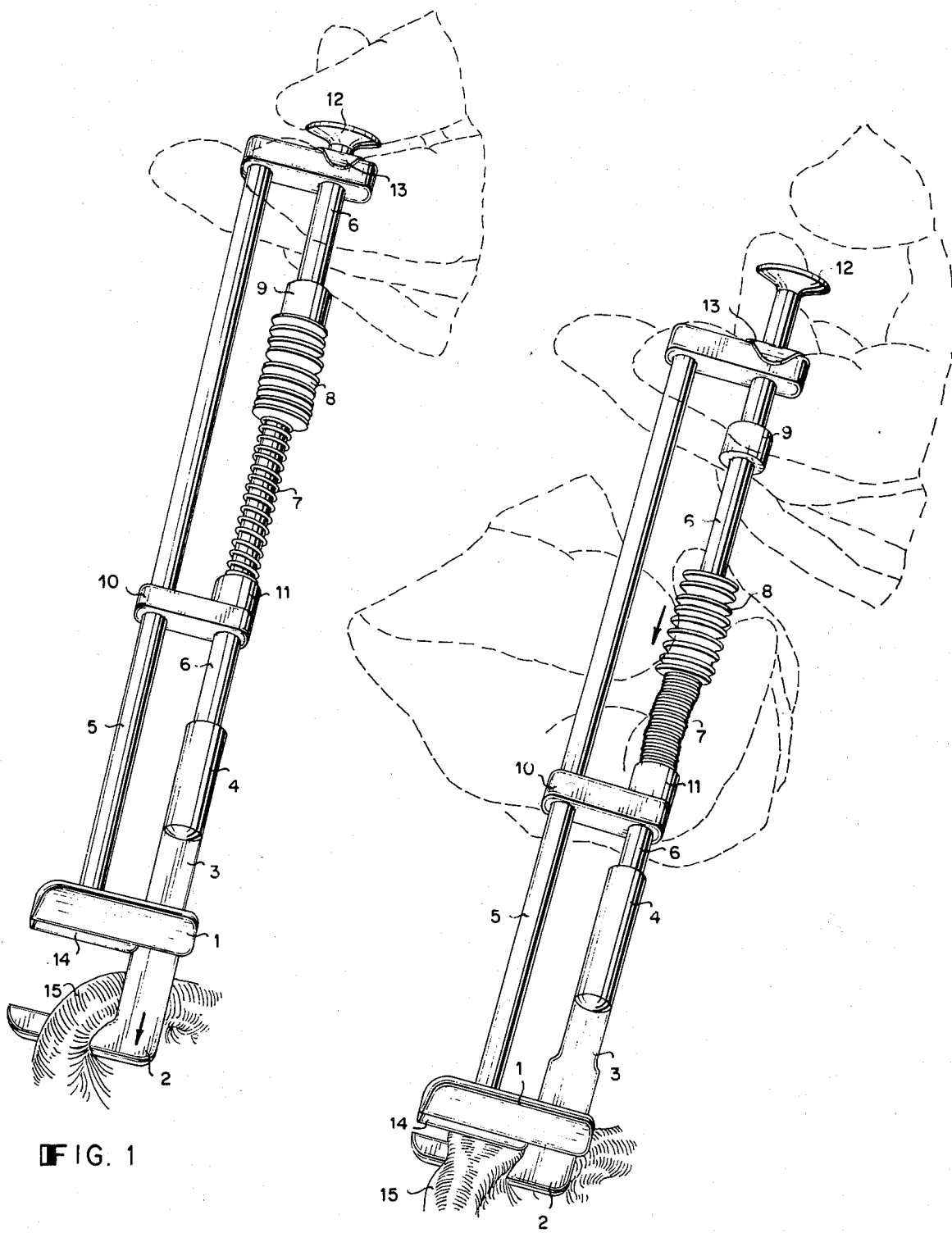
FIG. 1 is a prospective view of the instrument with the jaws of the guillotine open and a blood vessel resting on the bottom jaw which we refer to as the hammer of the guillotine.
FIG. 3 shows also in perspective the movement of the two hands of the user with one hand releasing the downward pressure which kept the jaws of the guillotine from closing. The other hand meanwhile is compressing the spring member which is located about a central rod or core which connects to the hammer of the guillotine.

Turning first to FIG. 1 of the drawing there is shown a device which comprises an anvil 1 and a hammer 2 which is slideably attached to a slider arm 3 which passes through a slot in the anvil 1 so that the two members are constantly aligned. The slider has a protuberance or a stop member 4 which limits the degree to which the jaws of the guillotine can be opened. The anvil member is controlled by a guide arm 5 which passes through an alignment piece 10 which has one end thereof attached to a central rod 6 for holding the hammer while the other end of the alignment piece 10 is fixably attached to the guide 5. Surrounding the central rod for the hammer member there are a series of springs. The first or proximal spring 7 is forced against a retainer 11 which is interposed between the proximal spring 7 and the alignment piece 10. The central rod is free to slide upward or downward in response to finger pressure exerted to the rod by a finger pressure button 12. While the device operates so that the finger gripper knob 13 is held firmly between the forefinger and the second finger the guide for the impact blade anvil 5 is also clutched between the ends of the forefinger and the second finger and the spring is first compressed by a movement of the other hand of the user and then released to impact against the shock knob of the central rod 9.

The impact of the distal spring 8 against the shock knob 9 of the central rod causes a wave of shock to travel down the central rod 6 and to be conveyed to the hammer 2 and transmitted from the hammer into the blood vessel 15 which presses against the blade 14 of the anvil 1. This causes the internal cutting or cleavage of the blood vessel.

It is essential to recognize in the present invention that the impact of the blade 14 which is a dull blade and physically attached to the anvil 1 is controlled by the level of shock or impact which is conveyed thereto by the collision of the spring released against the shock knob 9. It is clear that this shock or impact is sufficient to cleave the inner layer of the blood vessel but insufficient to cleave the outer layers of musculature which surround the same.

While the embodiments described in the drawing are intended to illustrate the invention it is within the scope of the invention to encompass all the variations related thereto and consequently all variations on this concept are considered to be within the scope of the appended claims.

I claim:

1. A fracture device for the selective fracture of the inner lining of a blood vessel without severing the surrounding outer layer of the vessel which comprises in combination (a) an anvil member 1 having a dull blade affixed thereto supported on a guide arm 5 acting as the superior member of said fracture device and (b) an inferior hammer member 2 having a handle connected to the anvil member said hammer member positioned in register with said anvil member and spring loaded by a spring means positioned between the handle and the guide arm, said anvil and hammer opposingly interconnected by means of a slider arm 3 to work in cooperation whereby a blood vessel interposed therebetween can be partially fractured by a shock imparted to the hammer by a controlled compression of the said spring means and subsequent release of the same causing said hammer to force the blood vessel against the dull blade of the anvil and cutting the inner lining of the same while not cutting the outer layer thereof.

2. A device according to claim 1 wherein the spring means in the handle is composed of two separate springs, one proximal and one distal to the hammer means.

3. A device according to claim 2 wherein the proximal spring means is a greater length than the distal spring means.

* * * * *